United States Patent [19]

Dirk et al.

[11] Patent Number: 5,670,110
[45] Date of Patent: Sep. 23, 1997

[54] METHOD FOR MAKING THREE-DIMENSIONAL MACROSCOPICALLY-EXPANDED WEBS HAVING IMPROVED FUNCTIONAL SURFACES

[75] Inventors: Raymond John Dirk, Cleves; Nicholas Albert Ahr, Cincinnati, both of Ohio

[73] Assignee: The Procter & Gamble Company, Cincinnati, Ohio

[21] Appl. No.: 576,610

[22] Filed: Dec. 21, 1995

[51] Int. Cl.[6] .................... B29C 67/08; B29C 69/02
[52] U.S. Cl. .................... 264/504; 264/131; 264/164; 425/326.1; 425/387.1; 425/90
[58] Field of Search .................... 264/504, 131, 264/164; 425/290, 326.1, 387.1, 90

[56] References Cited

U.S. PATENT DOCUMENTS

| | | | |
|---|---|---|---|
| 3,929,135 | 12/1975 | Thompson | 128/287 |
| 3,965,906 | 6/1976 | Karami | 128/287 |
| 3,967,623 | 7/1976 | Butterworth et al. | 128/287 |
| 4,151,240 | 4/1979 | Lucas et al. | 264/504 |
| 4,214,945 | 7/1980 | Lucas et al. | 156/634 |
| 4,311,745 | 1/1982 | Civardi | 428/91 |
| 4,342,314 | 8/1982 | Radel et al. | 128/287 |
| 4,377,544 | 3/1983 | Rasmussen | 264/164 |
| 4,508,256 | 4/1985 | Radel et al. | 228/152 |
| 4,585,449 | 4/1986 | Karami | 604/378 |
| 4,609,518 | 9/1986 | Curro et al. | 264/504 |
| 4,628,857 | 12/1986 | Coningsby | 118/406 |
| 4,629,643 | 12/1986 | Curro et al. | 428/131 |
| 4,655,757 | 4/1987 | McFarland et al. | 604/366 |
| 4,695,422 | 9/1987 | Curro et al. | 264/504 |
| 4,725,473 | 2/1988 | Van Gompel et al. | 428/156 |
| 4,741,941 | 5/1988 | Englebert et al. | 428/71 |
| 4,743,483 | 5/1988 | Shimizu et al. | 428/89 |
| 4,772,444 | 9/1988 | Curro et al. | 264/557 |
| 4,778,644 | 10/1988 | Curro et al. | 264/557 |
| 4,839,216 | 6/1989 | Curro et al. | 428/134 |
| 4,878,825 | 11/1989 | Mullane et al. | 425/290 |
| 5,058,247 | 10/1991 | Thomas et al. | 24/448 |
| 5,116,563 | 5/1992 | Thomas et al. | 264/167 |
| 5,124,111 | 6/1992 | Keller et al. | 264/112 |
| 5,128,082 | 7/1992 | Makoui | 264/112 |
| 5,158,819 | 10/1992 | Goodman, Jr. et al. | 428/131 |
| 5,180,534 | 1/1993 | Thomas et al. | 264/145 |
| 5,229,186 | 7/1993 | Tribble et al. | 428/156 |
| 5,230,851 | 7/1993 | Thomas | 264/145 |
| 5,318,741 | 6/1994 | Thomas | 264/145 |
| 5,431,643 | 7/1995 | Ouellette et al. | 604/385.1 |
| 5,441,691 | 8/1995 | Dobrin et al. | 264/504 |
| 5,454,801 | 10/1995 | Lauritzen | 604/378 |

FOREIGN PATENT DOCUMENTS

| | | |
|---|---|---|
| 72/4910 | 4/1973 | South Africa. |
| 282447 | 5/1928 | United Kingdom. |
| WO 93/19715 | 10/1993 | WIPO. |

*Primary Examiner*—Catherine Timm
*Attorney, Agent, or Firm*—William Scott Andes; E. Kelly Linman; Jacobus C. Rasser

[57] ABSTRACT

The present invention provides a process for forming a three-dimensional, macroscopically-expanded, fluid pervious web having an improved functional surface comprised of a sheet of polymeric material having a first surface and a second surface. A plurality of discrete deposits of a water resistant resinous material having a pre-determined open time are deposited on the first surface of the sheet. The deposits of resinous material are drawn upwardly from the first surface of the sheet to form corresponding fibrils during the open time. After resinous material has cured, the sheet is fed onto a forming structure having opposed surfaces such that the sheet is in contact with the forming structure. The forming structure exhibits a multiplicity of apertures which place the opposed surfaces of the forming structure in fluid communication with one another. A fluid pressure differential is applied across the thickness of the sheet which is sufficiently great as to cause the sheet to rupture in those areas coinciding with the apertures in the forming structure and to conform with the forming structure while substantially maintaining the orientation of the fibrils. The priming and drawing steps are preferably accomplished via a screen printing roll, and the fluid pressure differential preferably comprises a high pressure jet of liquid.

20 Claims, 3 Drawing Sheets

METHOD FOR MAKING THREE-DIMENSIONAL MACROSCOPICALLY-EXPANDED WEBS HAVING IMPROVED FUNCTIONAL SURFACES

FIELD OF THE INVENTION

The present invention relates to a method for making three-dimensional, macroscopically-expanded, fluid pervious webs particularly suited for use in a disposable absorbent article, such as a diaper, sanitary napkin, panty liner, incontinence pad, or the like. More particularly, the present invention relates to a method for making such webs which also include an improved, functional textured surface so as to be suitable for use as a topsheet on such a disposable absorbent article.

BACKGROUND OF THE INVENTION

It has long been known in the disposable absorbent article art that it is extremely desirable to construct absorptive devices such as disposable diapers, catmenials, sanitary napkins, bandages, incontinent briefs, and the like, presenting a dry surface feel to the user to improve wearing comfort and to minimize the development of undesirable skin conditions due to prolonged exposure to moisture absorbed within the article.

Recently, formed film materials having improved surface characteristics have been developed to provide the desirable fluid handling characteristics of formed film materials as well as visual and tactile characteristics which are perceived as less plastic-like. Materials of this variety are described in greater detail in commonly-assigned, co-pending U.S. patent application Ser. No. 08/494,273, filed Jun. 23, 1995 in the names of Ahr and Thomas, entitled "Absorbent Device with Improved Functional Surface", the disclosure of which is hereby incorporated herein by reference.

Although formed film webs provided with surface texture features as described therein are capable of providing desirable visual and tactile attributes, the process exemplified therein relied upon the use of pre-formed formed fill materials as the substrate upon which the fibrils were printed and cured. Since the printing processes therein described were inherently topographical in nature, i.e., deposition was accomplished by bringing one surface of the web into contact with a printing screen or roll, fibrils were only deposited on the uppermost surface of the formed film web. In addition, the size, pattern density, and orientation of the fibrils which could be deposited upon the formed film are limited by the comparatively small upper surface area of the formed film and by the flexibility and compressibility of the three-dimensional, macroscopically-expanded structure.

Accordingly, it would be desirable to provide an improved manufacturing process for producing formed film materials with improved functional surfaces which permits greater flexibility in terms of the surface features which may be provided and consequently a greater range of visual and tactile properties.

It would also be desirable to provide an improved manufacturing process for producing formed fill materials having improved functional surfaces which may be practiced readily, reliably, and economically.

SUMMARY OF THE INVENTION

The present invention provides a process for forming a three-dimensional, macroscopically-expanded, fluid pervious web having an improved functional surface comprised of a sheet of polymeric material having a first surface and a second surface. A plurality of discrete deposits of a water resistant resinous material having a pre-determined open time are deposited on the first surface of the sheet. The deposits of resinous material are drawn upwardly from the first surface of the sheet to form corresponding fibrils during the open time. After resinous material has cured, the sheet is fed onto a forming structure having opposed surfaces such that the sheet is in contact with the forming structure. The forming structure exhibits a multiplicity of apertures which place the opposed surfaces of the forming structure in fluid communication with one another. A fluid pressure differential is applied across the thickness of the sheet which is sufficiently great as to cause the sheet to rupture in those areas coinciding with the apertures in the forming structure and to conform with the forming structure while substantially maintaining the orientation of the fibrils.

The printing and drawing steps are preferably accomplished via a screen printing roll, and the fluid pressure differential preferably comprises a high pressure jet of liquid.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify like elements, and wherein:

DETAILED DESCRIPTION OF THE INVENTION

While the present invention will be described in the context of producing materials particularly suited for use in disposable absorbent articles, more particularly in the context of sanitary napkins, the present invention is in no way limited to such applications. To the contrary, the present invention may be practiced to great advantage whenever it is desired to produce three-dimensional, macroscopically-expanded webs not previously obtainable using prior art web forming processes.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad. A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

General Description of the Representative Absorbent Article

Figure 1:
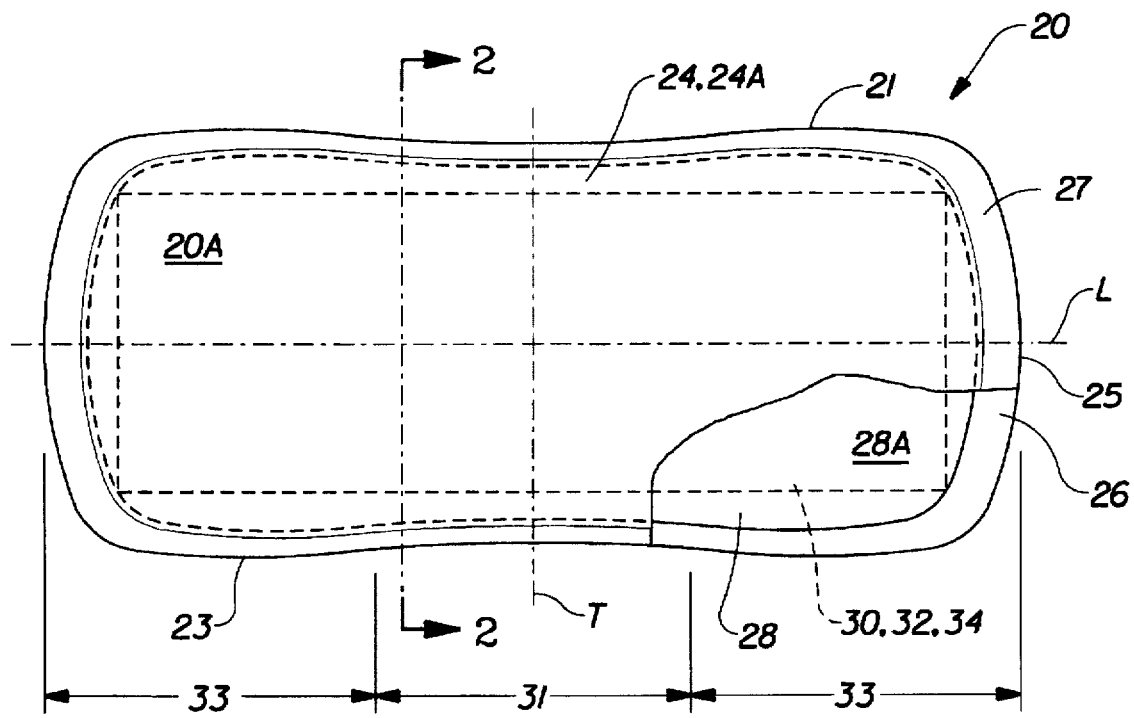
FIG. 1 is a top plan view, partially sectioned, of a preferred absorbent article configuration in the form of a sanitary napkin incorporating a fluid pervious web according to the present invention.

FIG. 1 is a plan view of the representative absorbent article, sanitary napkin 20, in its flat-out state with portions of the structure being cut-away to more clearly show the construction of the sanitary napkin 20 and with the portion of the sanitary napkin 20 which faces or contacts the wearer, oriented towards the viewer. As shown in FIG. 1, the sanitary napkin 20 preferably comprises a liquid pervious topsheet 24, a liquid impervious backsheet 26 joined with the topsheet 24, an absorbent core 28 positioned between the topsheet 24 and the backsheet 26, and attachment means 30 for releasably attaching the sanitary napkin 20 to a wearer's undergarment.

The sanitary napkin 20 has two surfaces, a body-contacting surface or "body surface" 20A and a garment surface 20B. In a similar manner each component comprising the sanitary napkin 20 may have a body surface designated by the reference number for the component with an appended A and a garment surface designated by the reference number for the component and an appended B. The sanitary napkin 20 is shown in FIG. 1 as viewed from its body surface. The body surface 20A is intended to be worn adjacent to the body of the wearer while the garment surface 20B is on the opposite side and is intended to be placed adjacent to the wearer's undergarments when the sanitary napkin 20 is worn. The sanitary napkin 20 has two centerlines, a longitudinal centerline L and a transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

FIG. 1 also shows that the sanitary napkin 20 has a periphery 21 which is defined by the outer edges of the sanitary napkin 20 in which the longitudinal edges are designated 23 and the end edges are designated 25. A central region 31 is disposed between two end regions 33. The end regions 33 extend longitudinally outwardly from the edges of the central region 31 about 12% to about 33% of the length of the sanitary napkin. A detailed description of a sanitary napkin having a central region 31 and the two end regions 33 is contained in U.S. Pat. No. 4,690,680, issued to Higgins on Sep. 1, 1987.

Figure 2:
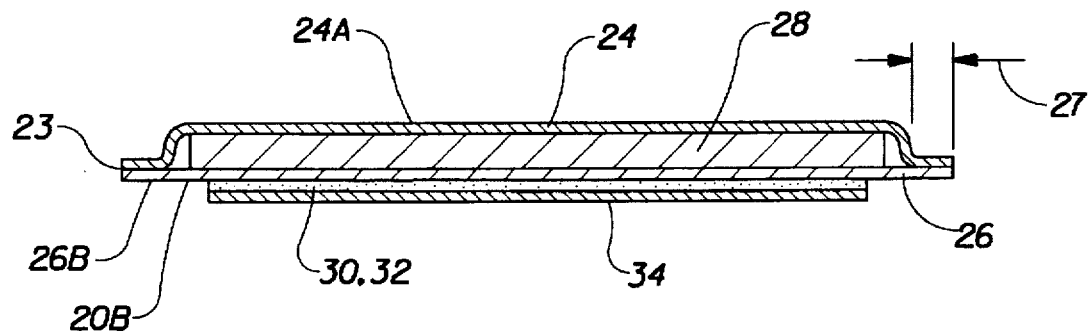
FIG. 2 is an enlarged cross-sectional view of the absorbent article of FIG. 1 taken along line 2—2.

While the topsheet, the backsheet, and the absorbent core may be assembled in a variety of well known configurations (including so called "tube" products or side flap products), preferred sanitary napkin configurations are described generally in U.S. Pat. No. 4,950,264, issued to Osborn on Aug. 21, 1990; U.S. Pat. No. 4,425,130, issued to Desmarais on Jan. 10, 1984; U.S. Pat. No. 4,321,924, issued to Ahr on Mar. 30, 1982; and U.S. Pat. No. 4,589,876, issued to Van Tilburg on Aug. 18, 1987. The disclosures of each of these patents are hereby incorporated herein by reference. FIG. 1 shows a preferred embodiment of the sanitary napkin 20 in which the topsheet 24 and the backsheet 26 have length and width dimensions generally larger than those of the absorbent core 28. The topsheet 24 and the backsheet 26 extend beyond the edges of the absorbent core 28 to thereby form at least a portion of the periphery 21. FIG. 2 depicts in greater detail the relationship between the various components of the sanitary napkin view from a cross-sectional perspective.

The representative absorbent article, sanitary napkin 20, is described in greater detail in commonly-assigned, co-pending U.S. patent application Ser. No. 08/561,989, Attorney's Docket No. 5877, filed Nov. 22, 1995 in the names of Christon and Ahr, entitled "Water Dispersible and Flushable Absorbent Article", the disclosure of which is hereby incorporated herein by reference. Suitable test and analytical methods for measuring various functional and characteristic attributes of such absorbent articles are also described in such application.

The Topsheet

In accordance with the present invention, the topsheet 24 of sanitary napkin 20 is compliant, soft feeling, and non-irritating to the wearer's skin. Further, the topsheet 24 is liquid pervious permitting liquids (e.g., menses and/or urine) to readily penetrate through its thickness. A preferred topsheet 24 comprises a three-dimensional, macroscopically-expanded, fluid pervious formed film web having a textured wearer-contacting surface of the type generally described in the aforementioned commonly-assigned, co-pending U.S. patent application Ser. No. 08/494,273, filed Jun. 23, 1995 in the names of Ahr and Thomas, entitled "Absorbent Device with Improved Functional Surface", the disclosure of which is hereby incorporated herein by reference.

Figure 4:
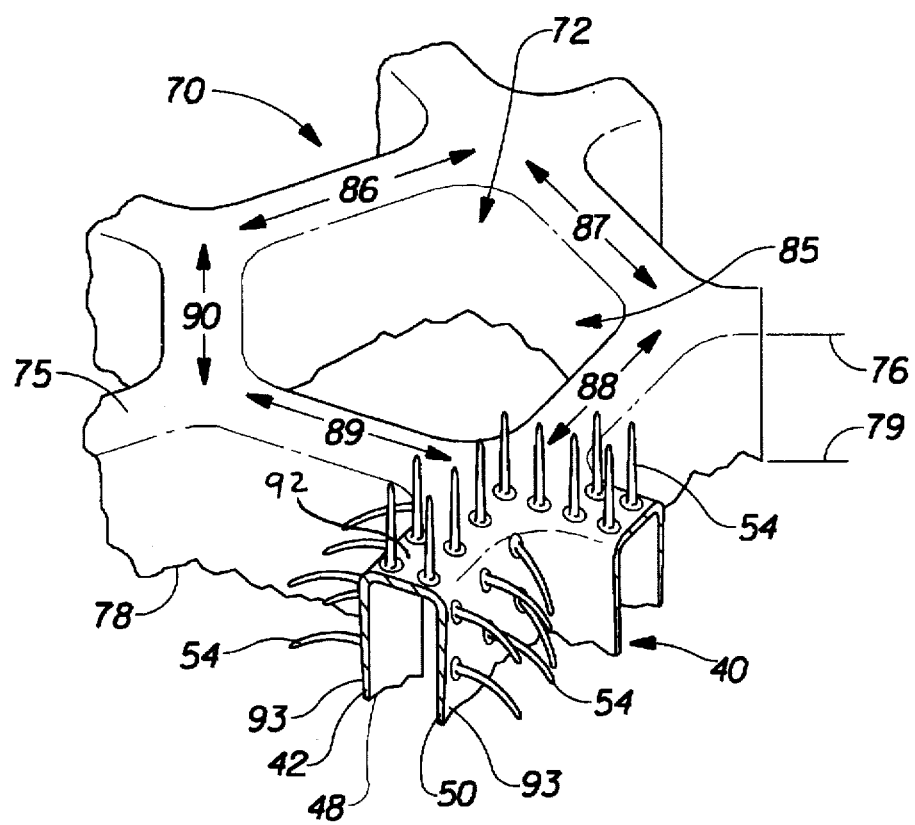
FIG. 4 is an enlarged, partially segmented, perspective illustration of a preferred embodiment of a textured film such as depicted in FIG. 3 which has been formed into a three-dimensional, macroscopically-expanded web by the process of the present invention.

FIG. 4 depicts in greater detail a topsheet 40 manufactured in accordance with the process of the present invention which is particularly well suited for use as a topsheet or acquisition layer in a sanitary napkin or other absorbent article, such as topsheet 24 depicted in FIGS. 1 and 2.

The material selected for the topsheet is preferably machinable and capable of being formed into a sheet such as sheet 42. Since the topsheet 40 is to be used in consumer products which contact the human body, the material utilized is preferably soft and safe for epidermal or other human contact. Preferred materials are polymeric materials including, but not limited to polyolefins, particularly polyethylenes, polypropylenes and copolymers having at least one olefinic constituent. Other polymeric materials such as polyester, nylon, copolymers thereof and combinations of any of the foregoing may also be suitable. While sheet 42 is shown as a film, the sheet may, if desired, be in the form of a nonwoven, microporous membrane, foam, etc. A presently preferred film material comprises a polyethylene film commercially available from Tredegar Film Products of Terre Haute, Ind., under the trade designation X-10038.

If desired, conventional amounts of agents may also be added to the polymeric matrix of the sheet 42. It is often desired to add agents to increase the opacity of the sheet. Whiteners, such as titanium dioxide and calcium carbonate may be used to opacify the sheet 42. It may also be desired to add other agents such as suffactants to impart a hydrophilic nature to the sheet 42. The sheet 42 may comprise a multilayer polymeric film such as those disclosed in commonly assigned U.S. Pat. No. 5,006,394 issued to Baird on Apr. 9, 1991 and U.S. Pat. No. 5,261,899 issued to Visscher et al. on Nov. 16, 1993, said patents being incorporated herein by reference.

FIG. 4 depicts in greater detail a topsheet 40 manufactured in accordance with the process of the present invention which is particularly well suited for use as a topsheet or acquisition layer in a sanitary napkin or other absorbent article, such as topsheet 24 depicted in FIGS. 1 and 2. The overall form/shape of the macroscopically expanded web 70 is generally in accordance with the teachings of commonly assigned U.S. Pat. No. 4,342,314, issued to Radel et al. on Aug. 3, 1982 and hereby incorporated herein by reference. Web 70 has been found suitable for use as a topsheet on a sanitary napkin. The term "macroscopically expanded", when used to describe three-dimensional webs of the present invention, refers to webs, ribbons, and films which have been caused to conform to the surface of a three-dimensional forming structure so that both surfaces thereof exhibit a three-dimensional pattern of surface aberrations corresponding to the macroscopic cross-section of said forming structure. The surface aberrations comprising said pattern being individually discernible to the normal naked eye, i.e., a normal naked eye having 20/20 vision unaided by any instrument that changes the apparent size or distance of an object or otherwise alters the visual powers of the eye, when the perpendicular distance between the viewer's eye and the plane of the web is about 12 inches. The term "fiber-like" as utilized herein to describe the appearance of webs of the present invention, refers generally to any fine-scale pattern of apertures, random or non-random, reticulated or non-reticulated, which connotes an overall appearance and impression of a woven or non-woven fibrous web when viewed by the human eye.

As can be seen in FIG. 4, the web's fiber-like appearance is comprised of a continuum of fiber-like elements, the opposed ends of each of the fiber-like elements are interconnected to at least one other of the fiber-like elements. In the embodiment disclosed in FIG. 4, the interconnected fiber-like elements form a pattern network of pentagonally shaped capillaries 72. The web 70, which exhibits a fiber-like appearance, embodies a three-dimensional microstructure extending from the web's uppermost or wearer-contacting surface 75 in plane 76 to its lowermost or absorbent pad-contacting surface 78 in plane 79 to promote rapid fluid transport from the uppermost surface 75 to the lowermost surface 78 of the web without lateral transmission of fluid between adjacent capillaries 72. As utilized herein, the term "microstructure" refers to a structure of such fine scale that its precise detail is readily perceived by the human eye only upon magnification by a microscope or other means well-known in the art.

Apertures 85 are formed by a multiplicity of intersecting fiber-like elements, e.g., elements 86, 87, 88, 89 and 90, interconnected to one another in the first surface of the web. Each fiber-like element comprises a base portion, e.g., base portion 92, located in plane 76. Each base portion has a sidewall portion, e.g., sidewall portions 93, attached to each edge thereof. The sidewall portions 93 extend generally in the direction of the second surface 78 of the web. The intersecting sidewall portions of the fiber-like elements are interconnected to one another intermediate the first and the second surfaces of the web and terminate substantially concurrently with one another in the plane 79 of the second surface.

In a particularly preferred embodiment, the interconnected sidewall portions terminate substantially concurrently with one another in the plane of the second surface to form apertures in the second surface 78 of the web. The network of capillaries 72 formed by the interconnected sidewall portions allows for free transfer of fluid from the first surface of the web directly to the second surface of the web without lateral transmission of the fluid between the adjacent capillaries.

This preferred formed film web is further provided with a multiplicity of fibrils 54 or "hairs" on the non-apertured portion of its body facing surface. These fibrils 54 improve the surface wetness characteristics of the topsheet 24 by separating the wearer's body from any bodily fluids that may remain on the body side surface of the topsheet 24A. Similarly, this separation from a wearer's body improves the acquisition rate for bodily fluids. The fibrils 54 also provide the body surface 24A with a pleasant, velour-like tactile feel.

The fibrils 54 preferably comprise a water resistant resinous material such as a hot melt resin blend, which is commercially available from Century International of Columbus, Ohio under the trade description CA-105. The fibril density can vary between about 500 fibrils per square inch (77 fibrils per square centimeter) to about 11,000 fibrils per square inch (1700 fibrils per square centimeter). Preferably, the fibril density is between about 3000 fibrils per square inch (450 fibrils per square centimeter) and about 5000 fibrils per square inch (775 fibrils per square centimeter). Fibril length can vary between about 0.003 inches (0.07 mm) to about 0.04 inches (1.0 mm). Preferably, the fibril length is between about 0.004 inches (0.1 mm) and about 0.01 inch (0.3 mm). The Applicants have found that choice of fibril length and fibril density allows the rewet characteristics, the acquisition characteristics and the tactile feel to be varied to achieve a desired balance of these characteristics.

In order to provide for adequate bonding of the fibrils to the film substrate material, since the resinous material is deposited as a liquid the surface energy and surface tension characteristics of the resinous material and film material, respectively, are preferably selected so that the resinous material adequately "wets" the film surface prior to curing. In this fashion, adequate contact area between the two materials is available for bonding such that the fibrils are firmly and reliably affixed to the film and thus are capable of surviving the range of manufacturing conditions and in-use conditions foreseen. Accordingly, polyethylene film materials having a critical surface tension of greater than about 34 dynes per centimeter (measured using the modified TAPPI test method described in the aforementioned commonly-assigned, co-pending U.S. patent application Ser. No. 08/561,989, Attorney's Docket No. 5877, filed Nov. 22, 1995 in the names of Christon and Ahr, entitled "Water Dispersible and Flushable Absorbent Article", the disclosure of which is hereby incorporated herein by reference) have been found to be suitable for use with the CA-105 water resistant resinous material described above.

Preferably, such fibrils are formed from a material which is generally hydrophobic in nature, or from a material which is rendered hydrophobic by known methods. This provides a wearer-contacting surface (the ends of the fibrils) which tends to repel fluids and provide a "dry" tactile impression, while the remainder of the web retains its hydrophilic characteristics to provide for enhanced acquisition properties. Such fibrils are described in greater detail in commonly-assigned, co-pending U.S. patent application Ser. No. 08/494,273, filed Jun. 23, 1995 in the names of Ahr and Thomas, entitled "Absorbent Device with Improved Functional Surface", the disclosure of which is hereby incorporated herein by reference.

The formed film web is preferably treated to form a web such that the body surface of the web provides a structure which exhibits a surface energy less than the surface energy of the intermediate portion. In a preferred embodiment, the treated web exhibits a plurality of regions of comparatively low surface energy which define surface energy gradients where they interface with higher surface energy web surfaces. For example, a silicone resin having a low surface energy can be applied to portions of the body surface 24A providing such regions of comparatively low surface energy. Webs having such surface energy gradients are fully described in U.S. patent application Ser. No. 08/442,935, filed on May 31, 1995 in the name of Ouellette, et al. the disclosure of which is incorporated herein by reference.

In a preferred embodiment of the present invention, at least portions of the body surface 24A of the topsheet 24 are hydrophilic so as to help liquid to transfer through the topsheet faster than if the body surface was not hydrophilic. Such a hydrophilic surface helps to diminish the likelihood that bodily fluids will flow off the topsheet rather than flowing into and being absorbed by the absorbent core. In a preferred embodiment, surfactant is applied to the body surface 24A of the topsheet 24 (e.g. by extrusion coating or spraying) before the fibrils are printed thereon. Alternatively, the body surface of the top sheet can be made hydrophilic by treating it with a surfactant such as is described in the above referenced U.S. Pat. No. 4,950,254, the disclosure of which is incorporated herein by reference.

Alternatively, if desired, the area provided with fibrils 54 may be of any desired shape, pattern, or coverage area and of either uniform or non-uniform density.

Figure 5:
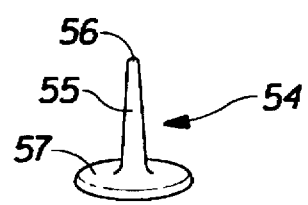
FIG. 5 is a greatly enlarged, perspective illustration of an individual fibril 54 such as depicted in FIG. 4.
Figure 3:
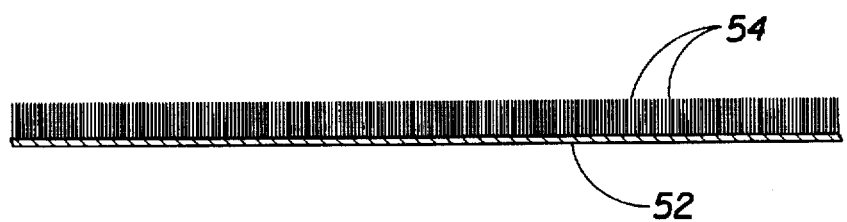
FIG. 3 is an enlarged cross-sectional view of a textured film material having a functional surface in accordance with the present invention.

FIG. 5 depicts in much greater detail the physical structure of a typical fibril 54 such as depicted in FIGS. 3 and 4. Fibril 54 preferably comprises a shaft portion 55 which extends from a base 57 to a tip 56. In formation, the resin material is deposited as base 57 and drawn upward to form shaft 55. The resin material abruptly separates from the resin remaining on the screen roll 110, forming tip 56, which is preferably slightly rounded. Fibrils are preferably constructed and arranged such that their respective bases 57 are spaced at least slightly apart, such that the underlying substrate therebetween is at least slightly exposed for acquisition purposes. In addition, the number and size of the fibrils must not be so great as to likewise obstruct the capillaries of the topsheet itself.

The resin material utilized to form the fibrils preferably cures or hardens quickly after the fibril has been formed to the desired height and/or configuration. In this fashion, the fibril is "locked in" before the resin can begin to collapse back downward toward the base 57 and the fibril loses its shape. This relatively short cure time, or "open time", is also conducive to comparatively higher web speeds as it ensures the fibrils are cured (i.e., the "open time" elapses) before subsequent web handling operations are undertaken. As discussed below, process techniques may be utilized to provide a reduced open time for a given resinous material.

If desired, the masking capabilities of the topsheet 24 can be enhanced by the addition of a dye or filler to the resinous material from which the fibrils 54 are made. Suitable masking agents include titanium dioxide and calcium carbonate. The fibrils 54 themselves, as well as the fillers aid in the masking of bodily fluids absorbed by the topsheet and the underlying absorbent core. The masking agent provides a clean and dry appearance by providing additional opacity to the topsheet as a whole, and particularly the upper surface thereof.

Fibrils 54 preferably have sufficient resilience by virtue of material properties, length, and thickness so as to be at least somewhat resistant to deflection toward the web surface when contacted by the wearer in use. If the fibrils collapse too readily, the effect of separation between the wearer and the fibrous hydrophilic substrate is dished and increasingly "wet" tactile impression may be encountered. Collapsed fibrils if too great in number may also prove to impair fluid acquisition by blocking apertures or pores in the substrate.

Fibrils 54 extend generally outwardly from the wearer-facing surface of the topsheet 24, as depicted generally in FIGS. 3 and 4. In a preferred configuration, a majority of the fibrils extend generally perpendicularly outwardly from the surface of the web, although at least some of the fibrils may extend outwardly at various angles.

As depicted in FIG. 4, a number of the fibrils 54 are present on the film surfaces which form the capillaries 72 of the formed film web 70. More particularly, such fibrils extend outwardly from the sidewalls and toward the center of the capillaries. Such fibrils provide a masking characteristic, i.e., they serve to obscure one's view downwardly through the capillaries and into underlying elements of an absorbent article, without unduly and excessively obstructing the passage of fluids through the capillaries. The provision of fibrils so oriented is made possible by the process of the present invention, as described below.

The Process

The preferred method for applying the resinous material to form the fibrils 54 is by a rotary screen printing method. It is to be understood, however, that other methods of printing or spraying such resinous projections are contemplated by the present invention. Such methods include spiral spraying, mist spraying, or line spraying, gravure printing, and flexographic printing. Rotary screen printing is the most preferred because the method is capable of producing the sizes and densities of fibrils desired and can also be performed at high web line speeds.

Figure 6:
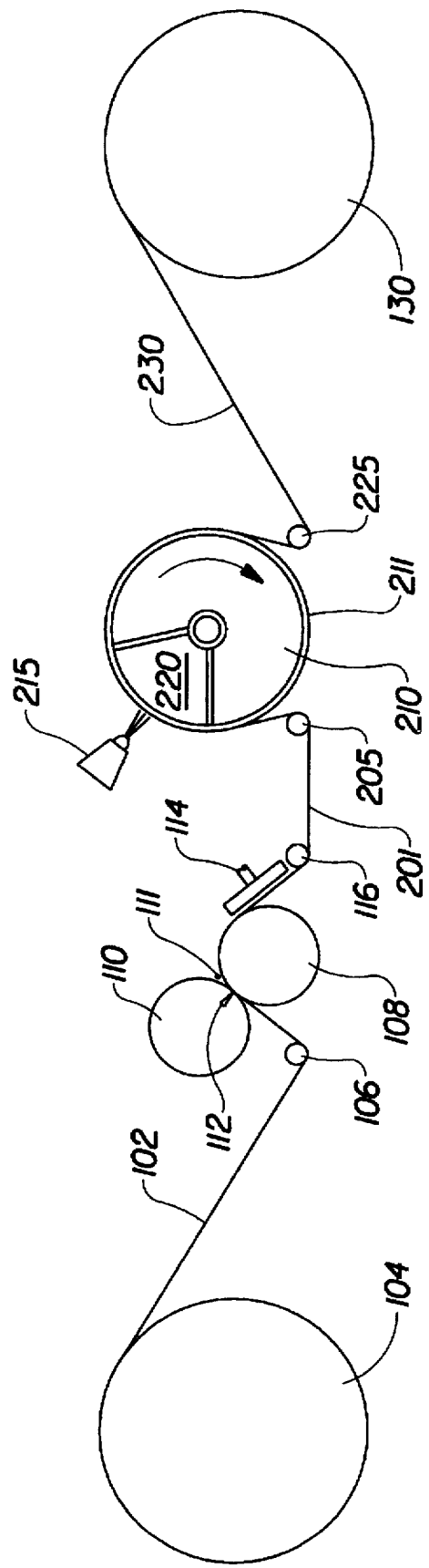
FIG. 6 is a schematic diagram of an apparatus suitable for forming the surface features of fluid pervious webs according to the process of the present invention.

Referring to FIG. 6, which illustrates a suitable resin application apparatus 100, the process for producing a three-dimensional, macroscopically-expanded web having an improved functional surface comprises the following steps. The substrate 102, having a mutually opposed first side and second side, is unwound from a parent roll 104. The substrate 102 is fed to a printing station comprising a backing roll 108, a print roll 110, and a feed roll 106. The backing roll 108 is juxtaposed with the printing roll 110 to form a nip therebetween. The printing roll 110 has a plurality of cells disposed about its periphery. In a preferred embodiment, the backing roll 108 comprises a backing roll rotatable about its longitudinal axis. Resinous material is delivered to the interior of the print roll 110 by a delivery mechanism (not shown) such as those well known in the art.

Tension control devices and tracking devices (not shown) well known in the art may also be used in this process, if such devices are necessary to insure an even coating of the resinous material across the entire transverse width of the substrate 102.

The resinous material is provided to the print roll 110 in a liquid state. If the resinous material is in a solid state at room temperature, it may be heated to a temperature above its melting point. Alternatively, resinous materials in a liquid state at room temperature may be utilized. For example, prepolymers comprising chemically reactive end groups may be utilized. In this case, after depositing the resinous material onto and into the substrate 102, a subsequent curing step is necessary to convert a liquid prepolymer into a solid state.

In the preferred embodiment of the process, the resinous material is heated to at least its melting point, causing the resinous material to be flowable.

The substrate 102 is transported, at a transport velocity, relative to the printing roll 110 and the backing roll 108, through the nip defined by the printing roll 110 and the backing roll 108. The flowable resinous material is disposed in the cells of the printing roll 110. The substrate 102 is transported through the nip in contacting relation with the cells of the printing roll 110. The printing roll 110 rotates about its longitudinal axis at a peripheral velocity, thereby applying the flowable resinous material from the cells of the printing roll 110 onto the substrate 102. Preferably, the coating weight of the resinous material 200 on the substrate 102 is between about 0.005 grams per square inch and about 0.075 grams per square inch.

Referring again to FIG. 6, the web velocity and the tangential velocity of the screen roll 110 are substantially the same. This means that the CA-105 resin is printed on the web 102 rather than being wiped across the web surface. By control of the screen pattern on the screen roll 110 and of rheology of the CA-105 when it is in its melted state, the CA-105 is printed as the fibrils 54 described above. The holes in the screen are small enough and the resinous material is of sufficient viscosity that the resinous material will not flow through the holes in the screen on its own. The doctor blade forces the resinous material to fill up the screen holes such that a meniscus of material hangs down from the screen toward the backing roll. As the screen roll and backing roll rotate, the screen contacts the substrate at the point of the backing roll and the meniscus of resinous material transfers from the screen holes onto the substrate. As the screen and web separate, the attraction or adhesion of the resin material for itself and for the screen surface cause a portion of the resin to be pulled upward away from the substrate until the separation distance exceeds the elastic limit of the resin material, causing the material to rupture and form the upper end of the fibril. The point of rupture may be controlled by using a hot wire/hot ribbon 111 placed at the desired distance from the printing roll 110 and the backing roll 108, as is known in the art. In this fashion, control of the point of rupture will generate fibrils of the desired caliper and shape.

With continuing reference to FIG. 6, the process according to the present invention may utilize a variety of types of printing rolls 110 including, but not limited to, a screen printing roll and a Gravure printing roll. In a preferred embodiment of the claimed invention, a screen printing roll is used. A screen printing roll is well known in the art, as illustrated by U.S. Pat. No. 4,628,857, issued to A. Robert Coningsby on Dec. 16, 1986, the disclosure of which is hereby incorporated herein by reference. Gravure printing rolls are also well known in the art as illustrated by U.S. Pat. No. 4,634,130, issued Feb. 17, 1988, to Sheath et al. and incorporated herein by reference to illustrate the general state of the art. A presently preferred print roll comprises a screen with a hexagonal interlocking mesh pattern having an average aperture diameter of 0.035 inches.

If desired, the printing roll 110 may have zones which do not print, hereinafter referred to as non-printing zones. As printing roll 110 preferably comprises a screen printing roll, the screen may have impermeable bars which block transmission of the resinous material through the screen at the positions of the bars. The areas of the printing roll from which resin is applied to the substrate 102 are referred to as the printing zone.

The non-printing zones may be generally longitudinally oriented, parallel to the axis of the printing roll. This arrangement produces generally cross machine direction oriented zones on the substrate 102 which do not contain fibrils. This arrangement may be utilized if desired to trim the resulting web into individual topsheets for disposable absorbent articles with the non-printed areas located at the margins of the absorbent articles, etc.

Alternatively, the non-printing zones may be generally circumferentially oriented, resulting in machine direction oriented zones of the substrate 102 not having the resinous material printed thereon. If desired, several repeating units of the web having zones with and without the resinous material may be juxtaposed together to form a resulting web which is relatively wide in the cross machine direction. The resulting web is then cut in the machine direction at positions corresponding to the desired zones to produce roll stock for use in later production. This arrangement provides the benefits of economy of scale in making disposable absorbent articles.

A doctor blade 112 is used to insure that the resinous material is evenly metered across the entire application face of the printing roll 110. The doctor blade 112 is held stationary as the printing roll 110 is rotated, allowing the doctor blade 112 to wipe the interior surface of the printing roll 110 and force the resinous material into the individual cells of the printing roll 110. The screen of printing roll 110 preferably has a thickness of approximately 4 to 7 millimeters.

The backing roll 108 is smooth and can either comprise a rotatable backing roll (either driven or freely-rotating) or a stationary surface. For the embodiment described herein, the printing roll 110 and the backing roll 108 are maintained in slightly spaced relation so as to avoid unduly compressing the substrate material.

The printing roll 110 is preferably heated to prevent premature solidification of the melted resinous material. A print roll temperature of about 250° F. has been found to work well with the resinous material and process conditions described herein.

A suitable resinous material is a hot melt resin blend that is available from Century International of Columbus, Ohio, under the designation CA-105.

The resinous material may be externally heated by known means (not shown) to maintain the material in a liquid state and at the proper temperature and viscosity. Typically the resinous material is maintained at a temperature slightly above the melting point. The temperature is considered to be at or above the melting point if the resinous material is partially or wholly in the liquid state. If the temperature is too low, it may not transfer from the printing roll 110 to the substrate 102, or subsequently, may not be suitable for printing. Conversely, if the temperature is too high, the material may not be viscous enough to be suitable for the printing process. However, the temperature should not be so high as to damage the substrate 102. For the embodiments described herein, the preferred temperature of the resinous material is from about 190° F. to about 250° F. at the point of application to the substrate 102. This temperature is above the melting point of the aforementioned CA-105 resinous material but below that at which a significant loss of viscoelasticity occurs.

Cooling air may optionally be provided from an air cooling system 114. The cooling air may be necessary to insure that the resinous material already applied to the substrate 102 has solidified before the web is removed from the printing roll 110, i.e., to reduce the effective "open time" of the resinous material and ensure the open time has elapsed before further manufacturing steps are accomplished. Alternatively, backing roll 108 can be chilled to "freeze" the resinous material into the desired fibril configuration. Guide rolls 128 and dancer roll 129 may be utilized to maintain the desired web tension.

Following application of the fibrils 54 to the sheet of material, the textured web 201 is fed around idler roll 205 and onto the surface of forming drum 210 about which a forming structure 211 continuously rotates at substantially the same speed as the incoming web. The web of film is driven by the forming drum 210. The web 201 is oriented such that the fibrils face away from the forming structure 211, and is of the general configuration of sheet 52 as discussed above with regard to FIG. 3. The sheet 52 depicted in FIG. 3 is therefore an intermediate configuration wherein the fibrils 54 have been applied but the sheet is still in a generally planar configuration prior to the macroscopically-expanding and aperturing process. It should be noted that the two portions of the process (the fibril application portion and the macroscopically-expanding and aperturing portion) may be accomplished one after the other in an essentially continuous multi-phase process or may be accomplished sequentially with an intervening storage/handling period. In the latter version of the process, the sheet 52 in the general form of FIG. 3 may be wound into a roll after the curing of the fibrils is completed and stored, to be later fed onto the forming structure to complete the formation process.

Forming structure 211 comprises a macroapertured surface, such as a patterned network of pentagonally-shaped capillaries, and is preferably constructed generally in accordance with the teachings of U.S. Pat. No. 4,342,314, issued to Radel and Thompson on Aug. 3, 1982, the disclosure of which is hereby incorporated herein by reference. Forming structure 211 is comprised of a plurality of individual photoetched lamina. The apertures in forming structure 211 may be of any desired shape or cross-section when the forming structure is fabricated using the laminar construction techniques generally disclosed in the aforementioned patent.

The forming drum 210 preferably includes an internally located vacuum chamber 220 which is preferably stationary relative to the moving forming structure 211. A pair of stationary baffles (not shown) approximately coinciding with the beginning and end of the vacuum chamber 220 are located adjacent the exterior surface of the forming structure. Intermediate the stationary baffles there is preferably provided means for applying a fluid pressure differential to the laminate web 201 as it passes over the vacuum chamber. In the illustrated embodiment, the fluid pressure differential applicator means comprises a high-pressure liquid nozzle 215 which discharges a jet of liquid, such as water, substantially uniformly across the entire width of web 201. Examples of methods for the production of formed materials using a high-pressure liquid stream are disclosed in U.S. Pat. No. 4,695,422, issued to Curro et al. on Sep. 22, 1987; U.S. Pat. No. 4,778,644, issued to Curro et al. on Oct. 18, 1988; and U.S. Pat. No. 4,839,216, issued to Curro et al. on Jun. 13, 1989, the disclosures of all of these patents being hereby incorporated herein by reference.

The water jet causes the web 201 to conform to the forming structure 211 and apertures the web 230 in the areas coinciding with the capillaries in forming structure 211. The pressure of the liquid stream, the tangential web speed through the fluid pressure differential, and the temperature of the liquid stream are preferably selected so as to achieve sufficient conformity of the web to the forming structure without causing detachment of the fibrils or excessive distortion of their orientation, or compromising the integrity of the sheet itself. Processing conditions which have proven satisfactory for manufacturing webs of the above-mentioned preferred materials are a water temperature of about 130° F., a water pressure of about 500 psi., and a tangential speed of about 340 feet per minute of the forming structure. Of particular importance is the selection of a water temperature sufficient to soften the film material for easier formation without overly softening the resinous material which comprises the fibrils, and hence causing excessive distortion or loss of the fibrils when subjected to the fluid pressure differential (high pressure fluid stream).

As discussed above, the surface energy and surface tension characteristics of the film material and the resinous material are preferably selected so as to provide a suitable degree of bonding between the respective materials so as to enable the fibrils to survive the formation process (being subjected to the fluid pressure differential) in substantially their original orientation.

As depicted in FIG. 4, as the film material is subjected to the fluid pressure differential as it passes over the forming structure the material stretches to some degree. Consequently, even if the fibrils are applied to the intermediate or precursor sheet 52 in generally uniform fashion (with regard to pattern density/spacing) as presently preferred, the stretching of the film causes the fibrils located near the second surface 78 of the web to be spaced farther apart in the capillary direction than the spacing of the fibrils located on or near the wearer-contacting surface 75. This additional characteristic of the formation process enables a substantially uniform pattern density to be selected vis-a-vis the design of the printing roll while reducing the likelihood that the fibrils located in the capillaries will unduly obstruct the capillaries themselves.

Following application of the fluid pressure differential to the web, the three-dimensional, macroscopically-expanded, apertured web 230 is removed from the surface of the forming structure 211 about an idler roll 225. The apertured web 230 may be utilized without further processing as a topsheet in an absorbent article. Alternatively, the apertured web 230 may be subjected to further processing, such as ring rolling, creping, or surface treatment as may be desired. Other post-formation treatments such as drying or shaking of the web to remove residual fluid/water from the formation process may also be undertaken.

The use of a fluid pressure differential to form the film after the fibrils have already been applied has been found to further enhance the visual and tactile properties of the resulting web. More particularly, the use of a fluid pressure differential subjects the fibrils to a degree of bending and flexing, i.e., it "works" the fibrils, such that their resistance to bending under an external force is at least somewhat lessened, at least some of the fibrils are at least slightly permanently deformed adding some randomness to their appearance, and the acuteness of any abrupt corners or ends of resinous material is also at least slightly reduced. The combination of resinous material printing of fibrils and forming the resulting film through the use of a fluid pressure differential thus provides a resulting web with a softer, more pleasing visual and tactile impression, and a greater degree of quietness under in-use conditions, than would be otherwise obtainable through the use of either process alone. The resulting process is also capable of being operated as a continuous integrated process, lending itself to suitable operating speeds and capacities for production of large quantities of such formed films in economical fashion.

While particular embodiments of the present invention have been illustrated and described, it would be obvious to those skilled in the an that various other changes and modifications can be made without departing from the spirit and scope of the invention. It is therefore intended to cover in the appended claims all such changes and modifications that are within the scope of this invention.

What is claimed is:

1. A process for forming s three-dimensional, macroscopically-expanded, fluid pervious web having an improved functional surface, said web being comprised of a sheet of polymeric material, said sheet having a first surface and a second surface, said process comprising the steps of:
   (a) printing a plurality of discrete deposits of a water resistant resinous material on said fist surface of said sheet, said resinous material having pre-determined open time;
   (b) drawing said deposits of said resinous material upwardly from said first surface of said sheet to form corresponding fibrils during said open time;
   (c) curing said resinous material;
   (d) feeding said sheet onto a forming structure having opposed surfaces such that said second surface of said sheet is in contact with said forming structure, said forming structure exhibiting a multiplicity of aperture which place the opposed surfaces of said forming structure in fluid communication with one another; and
   (e) applying a fluid pressure differential across the thickness of said sheet, said fluid pressure differential being sufficiently great to cause said sheet to rupture in those areas coinciding with said apertures in said forming structure and tow conform with said forming structure while substantially maintaining the orientation of said fibrils, wherein said fluid pressure differential causes said sheet to be drawn downwardly into said apertures, such that capillaries are formed in said sheet, said capillaries containing a plurality of fibrils extending therein.

2. The process of claim 1, wherein said sheet comprises a polyethylene film.

3. The process of claim 1, wherein said printing and drawing steps are accomplished via a screen printing roll.

4. The process of claim 1, wherein said resinous material comprises a silicone resin.

5. The process of claim 1, wherein said fibrils are provided at a density of between about 3000 fibrils per square inch and about 5000 fibrils per square inch.

6. The process of claim 1, wherein said resinous material is hydrophobic.

7. The process of claim 1, wherein said sheet is hydrophilic.

8. The process of claim 1, wherein said fluid pressure differential comprises a high pressure jet of liquid.

9. The process of claim 8, wherein said resinous material has a melting temperature which is higher than the temperature of said high pressure jet of liquid.

10. The process of claim 1, wherein said curing step is accomplished via an air cooling system.

11. The process of claim 1, wherein said curing step is accomplished by delaying the feeding of said sheet onto said forming structure until said open time has elapsed.

12. The process of claim 1, wherein said fibrils extend outwardly from said first surface of said sheet at least about 0.004 inches.

13. The process of claim 1, wherein said polymeric material exhibits a critical surface tension of at least about 34 dynes/cm.

14. The process of claim 1, wherein said discrete deposits of said resinous material are provided at a substantially uniform pattern density.

15. A process for forming a three-dimensional, macroscopically-expanded, fluid pervious web having an improved functional surface, said web being comprised of a sheet of polymeric material, said sheet having a first surface and a second surface, said process comprising the steps of:
   (a) printing a plurality of discrete deposits of a water resistant resinous material on said first surface of said sheet via a screen printing roll, said resinous material having a pre-determined open time;
   (b) drawing said deposits of said resinous material upwardly from said first surface of said sheet via said screen printing roll to form corresponding fibrils during said open time;
   (c) curing said resinous material via an air cooling system;
   (d) feeding said sheet onto a forming structure having opposed surfaces such that said second surface of said sheet is in contact with said forming structure, said forming structure exhibiting a multiplicity of apertures which place the opposed surfaces of said forming structure in fluid communication with one another, and
   (e) applying a fluid pressure differential comprising a high pressure jet of liquid across the thickness of said sheet, said fluid pressure differential being sufficiently great to cause said sheet to rupture in those areas coinciding with said apertures in said forming structure and to conform with said forming structure while substantially maintaining the orientation of hid fibrils, wherein said fluid pressure differential causes said sheet to be drawn downwardly into said apertures, such that capillaries are formed in said sheet, said capillaries containing a plurality of fibrils extending therein.

16. The process of claim 15, wherein said sheet comprises a polyethylene film.

17. The process of claim 15, wherein said resinous material comprises a silicone resin.

18. The process of claim 15, wherein said liquid comprises water.

19. A process for forming a three-dimensional, macroscopically-expanded, fluid pervious web having an improved functional surface, said web being comprised of a sheet of polyethylene film, said sheet having a first surface and a second surface, said process comprising the steps of:
   (a) printing a plurality of discrete deposits of a water resistant resinous material on said first surface of said sheet via a screen printing roll, said resinous material having a pre-determined open time, said resinous material comprising a silicone resin;

(b) drawing said deposits of said resinous material upwardly from said first surface of said sheet via said screen printing roll to form corresponding fibrils during said open time;

(c) curing said resinous material via an air cooling system;

(d) feeding said sheet onto a forming structure having opposed surfaces such that said second surface of said sheet is in contact with said forming structure, said forming structure exhibiting a multiplicity of apertures which place the opposed surfaces of said forming structure in fluid communication with one another; and (e) applying a fluid pressure differential comprising a high pressure jet of water across the thickness of said sheet, said fluid pressure differential being sufficiently great to cause said sheet to rupture in those areas coinciding with said apertures in said forming structure and to conform with said forming structure while substantially maintaining the orientation of said fibrils.

20. The process of claim 1, wherein said capillaries each include sidewalls and a center surrounded by the sidewalls, and wherein said plurality of fibrils contained within said capillaries extend outwardly from the sidewalls of said capillaries and toward the center of said capillaries.

* * * * *

UNITED STATES PATENT AND TRADEMARK OFFICE
CERTIFICATE OF CORRECTION

PATENT NO. : 5,670,110
DATED : September 23, 1997
INVENTOR(S) : R. J. Dirk et al.

It is certified that error appears in the above-identified patent and that said Letters Patent is hereby corrected as shown below:

Column 13, line 26, the "s" should read --a--.

Column 13, line 32, "fist" should read --first--.

Column 13, line 33, "having pre-determined" should read --having a pre-determined--.

Column 13, line 43, "aperture" should read --apertures--.

Column 13, line 50, "tow" should read --to--.

Column 14, line 49, "hid" should read --said--.

Signed and Sealed this

Twenty-seventh Day of March, 2001

Attest:

NICHOLAS P. GODICI

Attesting Officer

Acting Director of the United States Patent and Trademark Office